United States Patent
Gelbin et al.

[19]

[11] Patent Number: 5,659,060

[45] Date of Patent: Aug. 19, 1997

[54] PROCESS FOR MAKING ARYL FLUOROPHOSPHITES USEFUL AS STABILIZERS

[75] Inventors: Michael E. Gelbin, Fords; Michael H. Fisch, East Wayne; R. David Peveler, Woodcliff Lake, all of N.J.

[73] Assignee: Witco Corporation, Greenwich, Conn.

[21] Appl. No.: 745,005

[22] Filed: Nov. 7, 1996

[51] Int. Cl.$^6$ .................................................. C07F 9/146
[52] U.S. Cl. ................................................... 558/140
[58] Field of Search ............................... 558/140

[56] References Cited

U.S. PATENT DOCUMENTS

| | | | |
|---|---|---|---|
| 2,614,116 | 10/1952 | Lange et al. | 558/140 |
| 3,424,550 | 1/1969 | Wittmann | 558/140 |
| 4,912,155 | 3/1990 | Burton | 524/118 |
| 5,049,691 | 9/1991 | Burt et al. | 558/140 X |
| 5,061,818 | 10/1991 | Burton et al. | 558/140 X |

OTHER PUBLICATIONS

Database CAPLUS on STN, Chemical Abstracts Service, (Columbus, Ohio), Acc. No. 89–123823, Ao, M.S. et al. EP 312915, abstract, 1989. 1989.

*Primary Examiner*—Johann Richter
*Attorney, Agent, or Firm*—Scully, Scott, Murphy & Presser

[57] ABSTRACT

Disclosed is a process for making compounds of the formula

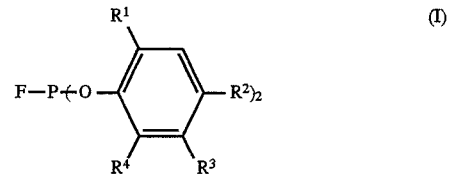

by reacting phosphorus trihalide with the corresponding phenol and fluorinating the resulting halophosphite intermediate, in the presence of a catalyst which comprises dimethylformamide.

6 Claims, No Drawings

PROCESS FOR MAKING ARYL FLUOROPHOSPHITES USEFUL AS STABILIZERS

FIELD OF THE INVENTION

The present invention relates to novel fluorophosphite compounds useful as stabilizers in organic materials such as organic polymers.

BACKGROUND OF THE INVENTION

Phosphites and other organic phosphorus compounds are used as antioxidants and stabilizers in organic materials such as organic polymers. In organic polymers such as polyolefin homopolymers and copolymers, they are generally considered better than phenolic antioxidants at elevated temperatures due to their ability to destroy hydroperoxides which decompose and lead to autooxidation chain reactions. Thus, organic phosphorus compounds are important for oxidative stability during numerous operations such as polyolefin extrusion. Additionally, in organic polymers such as polyvinyl chloride, organic phosphites are used to improve resistance of the resin to discoloration on exposure to the action of heat or light.

Thus, additives of the organic phosphite type are needed in larger amounts for processing organic polymers. Many of the antioxidants and stabilizers employed in organic materials have limited effectiveness or impart undesirable properties such as discoloration. Consequently, there exists a need for novel organic phosphites with improved antioxidant and stabilizing properties. The aryl fluorophosphites of the present invention allow organic materials to maintain excellent color and thermal stability.

Aryl fluorophosphites and their use as antioxidants in polymeric compositions have been disclosed in the patent literature. For instance, U.S. Pat. No. 4,912,155 discloses a large number of substituted phenyl and diphenyl compounds, including several dialkylphenyl fluorophosphites. However, the disclosure of this patent indicates that the synthesis of such compounds required a difficult, time-consuming process which also suffered from low yields. For instance, the synthesis of bis(2,6-di-t-butylphenyl) fluorophosphite required preparation and isolation of the corresponding chlorophosphite, and then fluorination of the chlorophosphite in a process which required a total of 61 hours reaction time and even then provided the target fluorophosphite in a yield of only 23%.

This patent also discusses preparation of bis-(2,4-di-t-butylphenyl) fluorophosphite by reaction of phosphorus trichloride and 2,4-di-t-butylphenol in the presence of a stoichiometric amount of triethylamine, followed without isolation of the intermediate by reaction with antimony trifluoride to convert the chloro groups to fluoro. This disclosure also involved a time-consuming process to the desired aryl fluorophosphite with a yield of only 55%.

Thus, there remains a need in this field for improvements in the processes of synthesizing aryl fluorophosphites. The identification of a catalyst or catalyst system would seem to be one way to meet this need, but catalysts which are satisfactory in all respects have not been found prior to the present invention. European Patent Application publication number 312,915 discloses triethylamine as a catalyst for synthesis of chlorophosphites, but as noted above, triethylamine used even in stoichiometric quantities did not lead to satisfactory reaction times and yields in the production of aryl fluorophosphites. U.S. Pat. No. 5,061,818 discloses the use of hydrogen halide salts of pyridine as a catalyst for similar syntheses, but pyridine is known to impart an extremely unpleasant odor to products containing it. Thus, a process using pyridine would require additional precautions to be taken in materials handling and process equipment. Also, additional purification steps would be required after formation of the fluorophosphite to avoid the presence of even the minutest amounts of pyridine in products to which the fluorophosphite is to be added.

BRIEF SUMMARY OF THE INVENTION

The present invention achieves these objectives and the additional advantages described herein. In general, the present invention comprises a process for making aryl fluorophosphite of the formula (I)

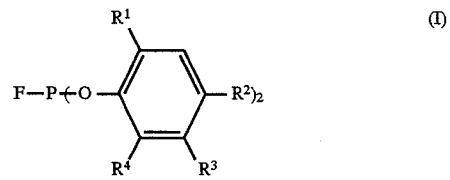

wherein $R^1$, $R^2$, $R^3$ and $R^4$ are the same or different and each is hydrogen or an aliphatic hydrocarbon radical containing 1 to 6 carbon atoms, by (a) reacting phosphorus trichloride, phosphorus tribromide or phosphorus triiodide with a phenolic compound of the formula (I-A)

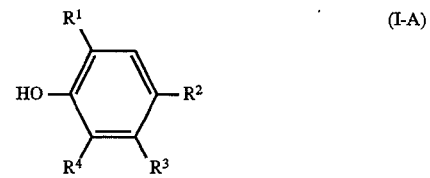

to form an intermediate of the formula (II)

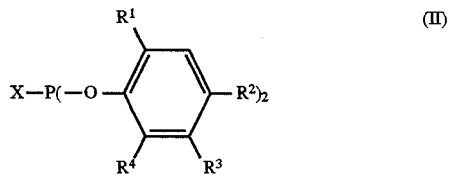

wherein X is Cl, Br or I,
and then (b) reacting said intermediate with a suitable fluorinating agent to form the aforementioned fluorophosphite compound (I) by transhalogenation, i.e. exchanging halogen bonded directly to phosphorus with a fluorine atom, wherein steps (a) and (b) are carried out in the presence of a catalytic amount of dimethylformamide. Yet another aspect of the present invention is the discovery that this two-step process can be carried out without requiring isolation of the intermediate product.

DETAILED DESCRIPTION OF THE INVENTION

In the first step of the process of the present invention, a phenolic compound is reacted with phosphorus trihalide. It should be understood throughout that the reaction can be carried out with one or a mixture of phenolic compounds of formula (I-A). The reaction is preferably carried out in an inert solvent such as toluene, by providing at least the two moles of phenol or substituted phenol per mole of phosphorus trihalide present as required by the stoichiometry of the reaction. Other liquid reaction media useful in this reaction include aprotic solvents such as tetrahydrofuran, benzene, xylene, heptane, octane, cyclohexane, and the like. The reaction is preferably carried out at moderately elevated temperature on the order of 20° C. to 300° C. The preferred reaction temperature is reflux temperature.

This reaction is carried out in the presence of a small but effective amount of an amine catalyst component for the reaction which contains dimethyl formamide. The dimethylformamide can be used alone, or combined with other amine catalysts examples of which are trialkyl amines, such as triethylamine; 1,5-diazabicyclo[4.3.0]non-5-ene; and 1,8-diazabicyclo[5.4.0]undec-7-ene. A preferred mixture is dimethylformamide and triethylamine, in a volume ratio of dimethylformamide: triethylamine of at least 1:10. Effective amounts of the amine catalyst component generally comprise less than one weight percent of the phenol reactant.

The progress of this first step can be monitored by assaying the reaction mixture periodically for the substituted phenol reactant or for the phosphorus trihalide.

This first reaction step forms an intermediate halogenated product of the formula (II)

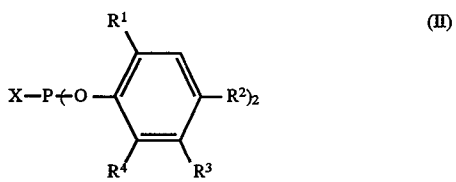

wherein X is Cl, Br or I.

In the second step of the desired reaction, this intermediate (II) is reacted with a fluorinating agent to substitute fluorine for the halogen atom in the intermediate of formula (II). Preferred fluorinating agents include ammonium fluoride, $NH_4F$, and antimony trifluoride, $SbF_3$. Other useful fluorinating agents include any fluoride salt capable of transhalogenating phosphorus bound chlorine, bromine, or iodine such as LiF, NaF, RbF, CsF, $CaF_2$, $KHF_2$, AgF, $SnF_4$, and $N(C_2H_5)_3 \cdot 3HF$ and the like.

The amount of the fluorinating agent added to the reaction mixture should be at least the stoichiometric amount required by the fluorination reaction based on the amount of compound (II) present. This transhalogenation reaction is also carried out in an inert aprotic solvent, such as those useful in the first step, a preferred example of which is toluene. Useful temperatures are in the range of 20° C. to 300° C., more preferably between 50° C. and 200° C. and most preferably at the atmospheric reflux temperature of the reaction mixture.

This reaction is also preferably catalyzed by an amine catalyst. Many of the amine catalysts useful in the first step of the process of the present invention are also effective in the second step, although triethylamine alone is not. It is a preferred embodiment of this invention to use dimethylformamide catalyst alone or in admixture with certain tertiary amine catalysts that—while commonly catalyzing the first step of the reaction—are known to lack catalytic activity in the transhalogenation step, such as triethylamine.

Thus, it is preferred, and is one of the useful aspects of the process of the present invention, that the two reaction steps (i.e. the formation of the halogenated intermediate (II), and the fluorination of this intermediate) can be carried out in sequence, and even in the same reaction vessel, without the need to isolate the intermediate (II) from its reaction mixture. Thus, the solvent and the amine catalyst added in the course of the first reaction step remain present for the second reaction step.

The progress of the second step in the reaction can be monitored by assaying the reaction mixture for the amount of the halogenated intermediate (II) present. If necessary, additional fluorinating agent can be added during the course of the reaction to promote complete conversion of the intermediate (II) to the desired final fluorophosphite product.

When the reaction to form the fluorophosphite product (I) has proceeded to completion, the reaction mixture is preferably filtered to remove solids, and the product (I) can be recovered from the filtrate after removing the solvent.

The process of the present invention produces the desired product (I) in much higher yield, and in much shorter reaction time, compared to the prior art processes. Yields typically 60% or higher, often 75% or higher, can be obtained. Reaction time for both steps is on the order of 5 hours or less.

The products of the present invention are useful as stabilizers for polymer compositions including polypropylene and vinyl halide resins, preferably polyvinyl chloride resins. Stabilization is provided against discoloration over time and against discoloration upon exposure to heat such as the elevated temperatures encountered in processing operations such as extrusion and molding.

The term "polyvinyl chloride" as used herein is inclusive of any polymer formed at least in part of the recurring group $(-CH_2CXCl-)_p$ and having a chlorine content in excess of 40%. In this formula, the X group can be either hydrogen or chlorine, and p is the number of units in each polymer chain. In polyvinyl chloride homopolymers, the X group is hydrogen, whereas in polyvinylidene chloride X is Cl. Thus, the terms "PVC" and "polyvinyl chloride" include not only polyvinyl chloride homopolymers but also after-chlorinated polyvinyl chlorides, as well as copolymers of vinyl chloride in a major proportion such as copolymers of vinyl chloride and vinyl acetate, copolymers of vinyl chloride with maleic or fumeric acids or esters, and copolymers of vinyl chloride with styrene. Also included are mixtures of polyvinyl chloride in major proportion with a minor proportion of other synthetic resins such as chlorinated polyethylene or copolymers of acrylonitrile, butylene and styrene.

The synthesis of products of formula (I) by the process of the present invention is described in the following Examples 1–4.

EXAMPLE 1

A carefully dried 500 mL three-necked round-bottomed flask was fitted with stirrer, condenser and addition funnel. The condenser was connected to an HCl scrubber. Then 51.6 g (250 mmol) 2,6-di-sec-butylphenol, 17.2 g (125 mmol) phosphorus trichloride ($PCl_3$), 60 mL dry toluene and a mixture of 1 mL triethylamine (TEA) and 0.1 mL dimethylformamide (DMF) was added to the flask. The reaction mixture was slowly heated to reflux and kept with stirring for 3.5 h. Subsequently, 7.1 g (40 mmol) $SbF_3$ was added. Refluxing was continued for 2 h. 10 g basic $Al_2O_3$ was added. The hot mixture was then filtered. The clear filtrate was freed from any volatiles under vacuum which was gradually increased to 5 mm Hg while the pot temperature was raised to 150° C. 47 g of corresponding fluorophosphite was isolated as an amber oil.

EXAMPLE 2

A dry 100 mL three-necked round-bottomed flask equipped with stirrer, condenser and addition funnel was charged with 8.9 g (50 mmol) 2,4-dimethyl-6-tert-butylphenol in 10 mL dry toluene and 1 mL of DMF/TEA mixture (1:10; v:v). 3.4 g (25 mmol) $PCl_3$ was added dropwise to the flask at room temperature. The reaction mixture was slowly heated to reflux and kept with stirring for 3.5 h. A sample taken for $^{13}$P-NMR analysis at this point showed 90% by area of chlorophosphite (II:X=Cl, $R^1$=$R^2$=Me; $R^3$=H;$R^4$=tert-Bu). The reaction mixture was then blanketed with nitrogen and 0.93 g of ammonium fluoride (25 mmol) was added, resulting in vigorous gas evolution. Refluxing was continued for 1.5 h. A sample taken for $^{31}$P-NMR analysis gave a corresponding fluorophosphite yield (I:$R^1$=$R^2$=Me; $R^3$=H;$R^4$=tert-Bu) of 96%. The hot mixture was then filtered to remove 1.4 g of colorless precipitate. The clear filtrate was evaporated to dryness in vacuo. After cooling, 7.1 g of an off-white solid was isolated.

EXAMPLE 3

A dry 100 mL three-necked round-bottomed flask equipped with stirrer, condenser and addition funnel was charged with 11.0 g (50 mmol) 2,4-di-tert-butyl-6-methylphenol, 10 mL dry toluene, 1 mL of DMF/TEA mixture (1:10/v:v), and 3.4 g (25 mmol) $PCl_3$ at room temperature. The reaction mixture was slowly heated to reflux and kept with stirring for 3.5 h. After the gas evolution subsided, the mixture was blanketed with nitrogen and 0.93 g of $NH_4F$ (25 mmol) was added. Refluxing was continued for 2 h. The hot mixture was then filtered through a glass frit. The clear filtrate was evaporated to dryness in vacuo, giving 8 g of crystalline product.

EXAMPLE 4

To a dry 100 mL three-necked round-bottomed flask fitted with magnetic stir bar, condenser, thermometer and addition funnel was charged 32.9 g (200 mmol) 2-tert-butyl-5-methylphenol dissolved in 10 mL dry toluene containing 0.1 mL 1,8-diazabicyclo[5.4.0]undec-7-ene. At room temperature 13.7 g (100 mmol) phosphorus trichloride was added dropwise over a period of 5 min. The mixture was heated to 70° C. and then kept with stirring for 90 min. Subsequently, the mixture was stirred at reflux for 90 min. A sample taken for $^{31}$P-NMR showed 68% intermediate chlorophosphite (II: X=Cl, $R^1$=tert-Bu, $R^3$=Me, $R^2$=$R^4$=H). The mixture was cooled to 80° C. while a slurry of 3.7 g (100 mmol) $NH_4F$ in 10 mL toluene was added. After further refluxing for 1 h, an additional amount of 0.4 g $NH_4F$ was added to the mixture. After an additional 30 min. of refluxing with stirring, the reaction mixture was filtered. The clear filtrate was freed from any solvent under vacuum and then triturated with acetonitrile. The trituration step yielded a white solid (6 g, m.p.=95°–98° C.) which was removed by filtration. This material analyzed as tris(2-tert-butyl-5-methylphenyl) phosphite. Then the acetonitrile solution was evaporated-off to dryness on a rotary evaporator, yielding 13.2 g of an amber oil which analyzed ($\delta_p$=133&122 ppm, doublet) as the target fluorophosphite FP-6.

The following Examples 5 and 6 show the performance of the aryl fluorophosphites of formula (I) as a stabilizer in polypropylene and polyvinyl chloride. They also present the performance of these compounds in comparison to prior art stabilizers, including other prior art fluorophosphite stabilizers. The data show that the fluorophosphite stabilizers of the present invention shown in formula (I) are comparable to or superior to other prior art stabilizers used for the same purpose.

EXAMPLE 5

Process Stabilization of Polypropylene at 475°

This example illustrates the stabilizing effectiveness of the aryl fluorophosphites of the present invention in combination with a representative phenolic antioxidant, in polypropylene as compared to other representative prior art compounds including prior art fluorophosphite.

The base formulation comprised unstabilized polypropylene (PROFAX®6501, Hercules Chemical) containing 0.1% by weight of tetrakis[methylene{3,5-di-tert-butyl-4-hydroxycinnamate}]methane as phenolic antioxidant. The test additives, at 0.2% by weight, were incorporated into polypropylene by dry blending or, when the additive was a liquid, using a minimum amount of heptane solvent, then removing the solvent by evaporating under reduced pressure. The stabilized resin formulation was extruded at 50 rpm from a 1 inch diameter extruder, (Killion single-screw) at 475° F.

After each of the 1st, 3rd and 5th extrusion, resin pellets obtained were compression molded into 60 mil thick plaques at 450° F., and specimen yellowness index (YI) determined on a Hunterlab Optical Sensor. Lower YI values indicate less discoloration.

After each of the first, third and fifth extrusion, the melt flow rate (in g/10 min.) was also determined by ASTM method D 1238 condition L on the pellets obtained from the extruder, using a Tinium Olson Extrusion Plastometer.

The results are shown in Table 2

TABLE 1

The fluorphosites which were tested and for which results are given in Table 2, are coded as follows:

| Code | Description |
|------|-------------|
| FP-1 | 3,9-difluoro-2,5,8,10-tetraoxa-3,9-diphosphaspiro[5.5]undecane |
| FP-2 | bis(2,6-di-sec-butylphenyl)fluorophosphite |
| FP-3 | FP-2(85%), Bis(2,6-di-sec-butylphenyl)chlorophosphite (7%), and FP$^v$-2(8%)* |
| FP-4 | bis(6-tert-butyl-2,4-dimethylphenyl) fluorophosphite |
| FP-5 | bis(2,4-di-tert-butyl-6-methylphenyl) fluorophosphite |
| FP-6 | bis(2-tert-butyl-5-methylphenyl) fluorophosphite |

* $^{31}$P-NMR percent

The results of these tests show that the FP-2 to FP-5 aryl fluorophosphites of the present invention protect polypropylene from degradation and discoloration far better than phenolic antioxidant alone or than does prior art stabilizer, including prior art fluorophosphite stabilizer PS-2.

TABLE 2

| | Extrusion #1 | | Extrusion #3 | | Extrusion #5 | |
|---|---|---|---|---|---|---|
| | Flow | | Flow | | Flow | |
| Additive | Rate g/10 min | Yellowness Index | Rate g/10 min | Yellowness Index | Rate g/10 | Yellowness Index |
| Base | 5.9 | 4.7 | 8.8 | 5.8 | 9.7 | 6.3 |
| Base + PS-1 | 3.7 | 6.6 | 4.1 | 9.0 | 4.5 | 11.3 |
| Base + PS-2 | 3.9 | 9.1 | 4.3 | 10.9 | 5.0 | 12.0 |
| Base + FP-1 | 5.0 | 2.6 | 6.1 | 3.2 | 6.8 | 4.7 |

TABLE 2-continued

|  | Extrusion #1 | | Extrusion #3 | | Extrusion #5 | |
| --- | --- | --- | --- | --- | --- | --- |
|  | Flow | | Flow | | | |
| Additive | Rate g/10 min | Yellow-ness Index | Rate g/10 min | Yellow-ness Index | Flow Rate g/10 | Yellow-ness Index |
| Base + FP-2 | 3.3 | 4.7 | 3.9 | 6.1 | 4.6 | 7.1 |
| Base + FP-3 | 3.5 | 4.5 | 3.7 | 5.5 | 4.7 | 6.6 |
| Base + FP-4 | 2.5 | 3.9 | 3.1 | 4.4 | 3.2 | 5.1 |
| Base + FP-5 | 2.8 | 5.3 | 3.3 | 6.2 | 3.7 | 7.7 |

PS-1: Tris(2,4-di-tert-butylphenyl)phosphite
PS-2: 2,2'-Ethylidene bis(4,6-di-tert-butylphenyl)fluorophosphite

EXAMPLE 6

Process Stabilization of Polyvinyl Chloride

This example illustrates the stabilizing effectiveness of the aryl fluorophosphites of the present invention in polyvinyl chloride. Thus, 100 parts by weight of polyvinyl chloride Oxy 225, 50 parts by weight of diisodecyl phthalate, five parts by weight of epoxidized soybean oil Drapex 6.8, 0.2 parts by weight of stearic acid, and two parts by weight of barium/zinc stabilizer Mark 6705 were throughly mixed with 1 part by weight of FP-2 and then homogenized by working on a roll mill heated at 160° C. The composition thus produced was removed in the form of a colorless sheet.

This sheet proves resistant to color changes upon being subjected to 190° C. for 70 min. A first control without FP-2 seriously discolored under these conditions. A second control with a representative phosphite stabilizer, octyl diphenyl phosphite, in place of FP-2, also used at one part by weight, displayed serious discoloration under these conditions, as well.

EXAMPLE 7

The hydrolytic stabilities of the aryl fluorophosphites listed were determined by placing 5 g samples into sealed humidity chambers equilibrated at 40 and 100% relative humidity, respectively. The samples were kept at ambient temperature and then monitored for solubility in $CDCl_3$ (deuterated chloroform), retention of free-flowing properties and melting point depression.

The results of these tests are shown in Table 3.

TABLE 3

| SAMPLE | % HYDROLYSIS AT 40% REL. HUMIDITY AFTER 3 WEEKS | % HYDROLYSIS AT 100% REL. HUMIDITY AFTER 1 WEEK |
| --- | --- | --- |
| PS-3* | 100 | 100 |
| FP-4 | 0 | 30 |
| FP-5 | 0 | 0 |

*3,9-bis(2,4-di-tert-butylphenyl)-2,5,8,10-tetraoxa-3,9-diphosphaspiro[5.5]undecane The results of these tests show the superior resistance to hydrolysis of the aryl fluorophosphites of the present invention compared with a prior art phosphite.

What is claimed is:

1. A process of making aryl fluorophosphite of the formula (I)

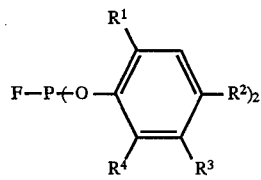

wherein $R^1$, $R^2$, $R^3$ and $R^4$ are the same or different and each is hydrogen or an aliphatic hydrocarbon containing 1 to 6 carbon atoms, comprising (a) reacting phosphorous trihalide selected from the group consisting of phosphorus trichloride, phosphorus tribromide, phosphorus triiodide, and mixtures thereof, with a phenolic compound selected from the group consisting of compounds of the formula

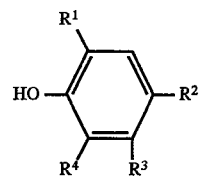

and mixtures thereof to form an intermediate of the formula (II)

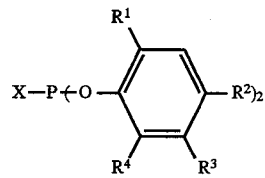

wherein X is Cl, Br or I, and then (b) reacting said intermediate of formula (II) with a fluorinating agent to form said product of formula (I), wherein steps (a) and (b) are carried out in the presence of a catalytically effective amount of a catalyst which comprises dimethylformamide.

2. A process according to claim 1 wherein step (b) is carried out without isolating said compound of formula (II) from the reaction product formed in step (a).

3. A process according to claim 1 wherein said fluorinating agent is selected from the group consisting of $NH_4F$, $SbF_3$, LiF, NaF, KF, RbF, CsF, $CaF_2$, $KHF_2$, AgF, $SnF_4$, $N(C_2H_5)_3 \cdot 3HF$, and mixtures thereof.

4. A process according to claim 1 wherein said catalyst is a mixture of dimethylformamide and triethylamine.

5. A process according to claim 4 wherein the ratio by volume of dimethylformamide to triethylamine is at least 1:20.

6. A process according to claim 1 wherein said catalyst comprises up to 5 wt.% of the phenolic compound which is reacted in step (a).

* * * * *

UNITED STATES PATENT AND TRADEMARK OFFICE
CERTIFICATE OF CORRECTION

PATENT NO. : 5,659,060
DATED : August 19, 1997
INVENTOR(S) : M. E. Gelbin, et al.

It is certified that error appears in the above-indentified patent and that said Letters Patent is hereby corrected as shown below:

Column 5, line 1: " $^{13}$P-NMR" should read -- $^{31}$P-NMR--

Column 6, line 29: "fluorphosites" should read --fluorophosphites--

Signed and Sealed this

First Day of September, 1998

Attest:

BRUCE LEHMAN

*Attesting Officer*  *Commissioner of Patents and Trademarks*